United States Patent [19]

Baggiolini et al.

[11] Patent Number: 5,120,722
[45] Date of Patent: Jun. 9, 1992

[54] TRIHYDROXY-CHOLECACLIFEROL AND TRIHYDROXY-ERGOCALCIFEROL FOR TREATING LEUKEMIA

[75] Inventors: Enrico G. Baggiolini; Andrew D. Batcho, both of North Caldwell; Gary A. Truitt, Passaic; Milan R. Uskokovic, Upper Montclair; Peter M. Wovkulich, Nutley, all of N.J.

[73] Assignee: Hoffmann-La Roche Inc., Nutley, N.J.

[21] Appl. No.: 495,519

[22] Filed: Mar. 19, 1990

Related U.S. Application Data

[63] Continuation of Ser. No. 109,962, Oct. 19, 1987, abandoned, which is a continuation of Ser. No. 682,125, Dec. 17, 1984, abandoned, which is a continuation-in-part of Ser. No. 578,160, Feb. 8, 1984, abandoned.

[51] Int. Cl.$^5$ .......................... A61K 31/59; C07J 9/00
[52] U.S. Cl. ..................................... 514/167; 514/168; 552/653
[58] Field of Search ................. 552/653; 514/167, 168

[56] References Cited

U.S. PATENT DOCUMENTS

| | | | |
|---|---|---|---|
| 3,741,996 | 6/1973 | DeLuca et al. | 552/541 |
| 3,880,894 | 4/1975 | DeLuca et al. | 552/653 |
| 3,907,843 | 9/1975 | DeLuca et al. | 552/541 |
| 4,022,768 | 5/1977 | Matsynaga et al. | 552/541 |
| 4,225,596 | 9/1980 | DeLuca et al. | 514/167 |
| 4,391,802 | 7/1983 | Suda et al. | 514/167 |
| 4,407,754 | 10/1983 | Barner et al. | 552/541 |
| 4,448,721 | 5/1984 | DeLuca et al. | 552/546 |
| 4,588,528 | 5/1986 | DeLuca et al. | 552/541 |
| 4,617,297 | 10/1986 | Boris | 514/167 |
| 4,728,643 | 11/1988 | Holick et al. | 514/167 |

FOREIGN PATENT DOCUMENTS 58-210017 12/1983 Japan.

OTHER PUBLICATIONS

Windholz et al., "The Merck Index", Merck Co. 9th Ed. p. 1289 (1979).
Frampton, et al., Inhibition of Human Cancer Cell Growth by 1,25-Dihydroxy-vitamin $D_3$ Metabolites, Cancer Research 43:4443,4447, 1983.
K. Schaefer, D. Von Herrath, "Vitamin D 1980—Eine Bestandsaufnahme".
Dokoh, et al., The Ovary:A Target Organ for 1,25-Dihydroxyvitamin $D_3$, Endocrinology 112: 200-206, 1983.
Reitsma, et al., Vitamin $D_3$ Regulates C-myc Oncogene Expression in HL-60 Leukemic Cells, J. Cell. Biol. 97(5):347a, 1983.
Murao, et al., Control of Macrophage Cell Differentiation in Human Promyelocytic HL-60 Leukemia Cells by 1,25-Dihydroxyvitamin $D_3$ and Phorbol-12-myristate-13-acetate, Cancer Research 43(8): 4989-4996, 1983.
Rigby, et al., 1,25-Dihydroxyvitamin $D_3$ Induces Granulocytic Differentiation and Myeloid Specific Antigens in the HL-60 Promyelocytic Leukemia Cell Line, Blood 62(5): 153a, 1983.
Shuna, et al., Biological Activity of 24,24-Difluoro-1α,25-Dihydroxyvitamin $D_3$-26,23 Lactone in Inducing Differentiation of Human Myeloid Leukemia Cells, Arch. Biochem. Biophys,220: 90-94, 1983.
Abe et al., Differentiation of Mouse Myeloid Leukemia Cells Induced by 1α,25-Dihydroxyvitamin $D_3$; Proc. Natl. Acad. Sci.; U.S.A. 78:4990-4994, 1981.
McCarthy et al., 1α,25-Dihydroxyvitamin $D_3$ Causes Granulocytes From Patients with Chronic Granylocytic Leukemia to Differentiate Into Myoctye-Macrophages, Exp. Hematol. 11(Suppl. 14):200, 1983.
Honma et al., 1α,25-Dihydroxyvitamin $D_3$ and 1α-hydroxyvitamin $D_3$ Prolong Survival Time of Mice Inoculated with Myeloid Leukemia Cells, Cell Biology, 80:201-204, 1983.
Kasukabe, et al., Control of Proliferating Potential of Myeloid Leukemia Cells During Long Term Treatment with Vitamin $D_3$ Analogues and Other Differentiation Inducers in Combination with AntiLeukemic Drugs, Cancer Res. 47(6):567-572, 1987.
Olsson et al., Induction of Differentiation of the Human Histocytic Lymphoma Cell Line U-937 by 1α,2-5-Dihydroxycholecalciferol, Cancer Research 43(12),5862-5867, 1983.
Eisman, et al., 1,25-Dihydroxyvitamin D Receptor in Breast Cancer Cells, Lancet, Dec. 22/29: 1335-1336, 1979.
Frampton, et al., Presence of 1,25-Dihdyroxyvitamin $D_3$ Receptors in Established Human Cancer Cell Lines in Culture, Cancer Research 42: 1116-1119, 1982.
Colston et al., 1,25-Dihdyroxyvitamin $D_3$ Receptors in Human Epithelial Cancer Cell Lines, Cancer Research 42: 856-859, 1982.
Sher et al., Whole Cell Uptake and Nuclear Localization of 1,25-Dihydroxycholecalciferol by Breast Cancer Cells in Culture, Biochem. J. 200:315-320, 1981.
Sato et al., Antitumor Effect of 1α,-Hydroxyvitamin $D_3$, Tohoku, J. Exp. Med., 138:445-446, 1982.
McCarthy et al., A Role for 1,25-Dihydroxyvitamin $D_3$ in Control of Bone Marrow Collagen Deposition? Lancet, Jan. 14: 78-80, 1984.
Eisman et al., Suppression of In Vivo Growth of Human Cancer Solid Tumor Xenografts, by 1,25-Dihydroxyvitamin $D_3$, Cancer Res. 47: 21-25, 1987.

*Primary Examiner*—C. Warren Ivy
*Assistant Examiner*—Celia Chang
*Attorney, Agent, or Firm*—George M. Gould; William S. Isgro; Ellen Ciambrone Coletti

[57] ABSTRACT

The compounds 1α,25(S), 26-trihydroxy-$\Delta^{22}$-cholecalciferol; 1α,25(R), 26-trihydroxy-$\Delta$>-cholecalciferol; 1α,25(S),26-trihydroxyergocalciferol, 1α,25(R),26-trihydroxyergocalciferol and pharmaceutical compositions comprising the compounds as well as methods of making and using these compounds are disclosed.

13 Claims, No Drawings

TRIHYDROXY-CHOLECACLIFEROL AND TRIHYDROXY-ERGOCALCIFEROL FOR TREATING LEUKEMIA

This is a continuation of application Ser. No. 07/109,962, filed Oct. 19, 1987; which is a continuation of Ser. No. 06/682,125, filed Dec. 17, 1984, now abandoned; which is a continuation-in-part of Ser. No. 578,160, filed Feb. 8, 1984, now abandoned.

BRIEF SUMMARY OF THE INVENTION

The invention relates to a process for the preparation of 1α,25(S) or (R),26-trihydroxycholecalciferol, 1α,25(S) or (R),26-trihydroxy-Δ$^{22}$-cholecalciferol or 1α,25(S) or (R),26-trihydroxyergocalciferol which comprises reacting the corresponding, specific epimer of the formula

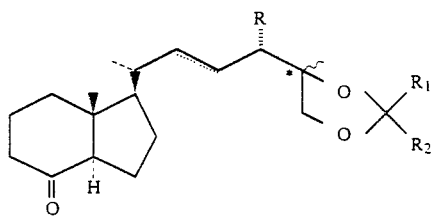

wherein R, R$_1$ and R$_2$, and the dotted (...) line, are as hereinafter described,
with a compound of the formula

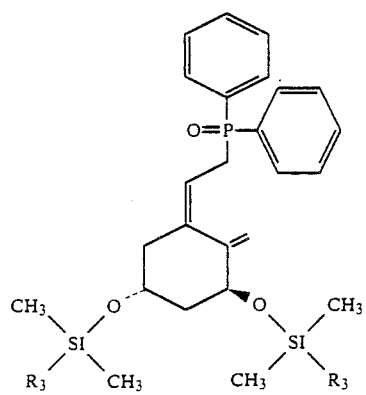

wherein R$_3$ is as hereinafter described.
to yield a compound of the formula

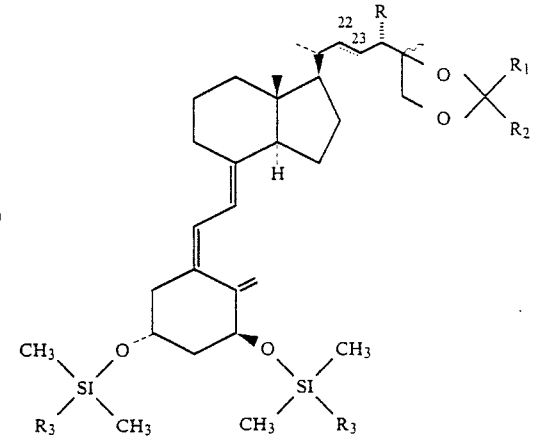

wherein R$_3$ is as hereinafter described.
removing the protecting groups from the resulting compound of formula IV and thereby obtaining the corresponding epimer of the formula

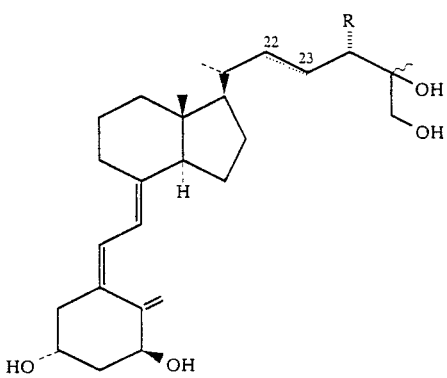

wherein the dotted (...) line between positions 22 and 23 represents an optional bond.

In another aspect, the invention relates to the 1α,25S,26trihydroxy-Δ$^{22}$-cholecalciferol, 1α,25R,26-trihydroxy-Δ$^{22}$-cholecalciferol, 1α,25S,26-trihydroxyergocalciferol, and 1α,25R,26-trihydroxyergocalciferol.

In yet another aspect, the invention relates to compounds of the formula

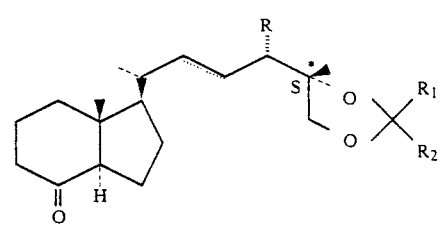

wherein the dotted (...) line represents an optional bond and R, R$_1$ and R$_2$ are as hereinafter described, and the *R epimers.

Detailed Description of the Invention

As used herein, the term "lower alkyl", alone or in combination, denotes a straight or branched-chain saturated hydrocarbon group Preferably containing from 1 to 6 carbon atoms, for example, methyl, ethyl, propyl, isopropyl, butyl, tert.butyl, pentyl and hexyl. The term "lower alkylene" denotes a straight or branched-chain organic radical derived from an unsaturated aliphatic hydrocarbon group preferably containing from 3 to 6 carbon atoms, for example, propylene, butylene and the like. The term "aryl" denotes phenyl or phenyl bearing one or more substituents selected from the group consisting of lower alkyl and lower alkoxy of 1 to 6 carbon atoms.

In the formulas represented herein, when substituents are illustrated as joined to the nucleus by a solid line (—◀) it indicates that the substituent is in the β-orientation, that is, above the plane of the molecule, a broken line (------) indicates that the substituent is in the α-orientation, that is, below the plane of the molecule, and a wavy line ($\sim$) indicates the α- or β-orientation.

It is understood that while the C-25 or C* epimers are prepared and discussed individually, mixtures of the C-25 or C* epimers are also with the scope of the invention.

The invention relates to a process for the preparation of 1α,25(S) or (R),26-trihydroxy-cholecalciferol, 1α,25(S) or (R),26-trihydroxy-Δ$^{22}$-cholecalciferol or 1α,25(S) or (R),26-trihydroxyergocalciferol of the formula

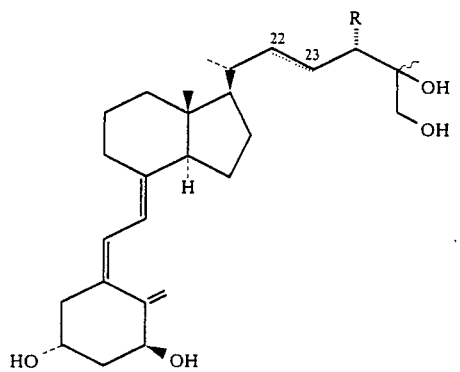

wherein the dotted (. . .) line between positions 22 and 23 represents an optional bond, and intermediates.

More particularly, the process for preparing a compound of formula I comprises reacting the corresponding epimer of the formula

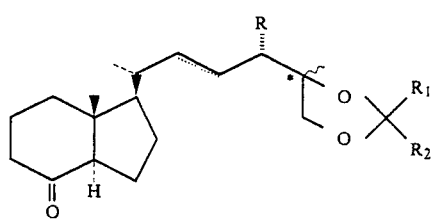

wherein R is hydrogen or methyl, $R_1$ and $R_2$ each, independently, is hydrogen, lower alkyl or aryl, or taken together are lower alkylene of from 3 to 6 carbon atoms and the dotted (. . .) line is an optional bond. with a compound of the formula

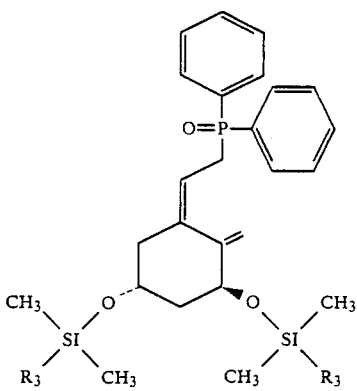

wherein $R_3$ is lower alkyl or aryl to yield the corresponding epimer of the formula

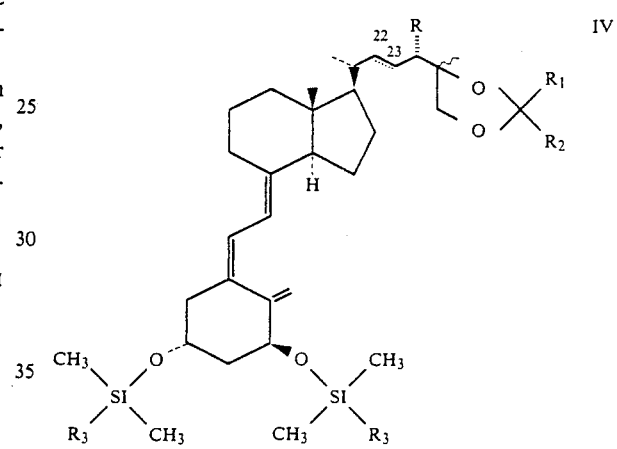

wherein $R_3$ is as previously described.

In accordance with the invention, a ketone of the formula II, wherein R, $R_1$ and $R_2$ are as described above, is reacted with a phosphine oxide of the formula III, wherein $R^3$ is as described above, which are known compounds or can be prepared according to known procedures, to yield a compound of formula IV wherein R, $R_1$, $R_2$ and $R_3$ are as described above. The reaction is carried out in the presence of a base in a conventional ether solvent, for example, tetrahydrofuran, dioxane or the like, under an inert atmosphere, for example, under argon or the like, at a temperature in the range of from about −80° C. to about −50° C. Exemplary of suitable bases are alkyl lithium compounds, such as, n-butyllithium and alkali metal dialkyl or disilyl amides. The compound of formula IV can be Purified, for example, by elution chromatography on silica gel.

The compound of formula IV is converted to the corresponding compound of formula I by removal of the hydroxyl derivatizing groups by treating the compound of formula IV with a deprotecting agent, for example, an alkanol, such as, ethanol or the like, or water in the presence of an acid. While any mineral acid or lower alkanoic or sulfonic acid may be used it is preferred to use a cationic ion exchange resin as a suspension in a lower alkanol. The corresponding compound of the formula I is isolated by removal of the solid cationic exchange resin by filtration and evaporation of the volatiles under reduced pressure.

The preparation of the trihydroxy Δ²²-cholecalciferols can be further illustrated as follows:

The process for the preparation of 1 α,25S,26-trihydroxy-Δ²²-cholecalciferol and 1 α,25R,26-trihydroxy-Δ²²-cholecalciferol of the formulas,

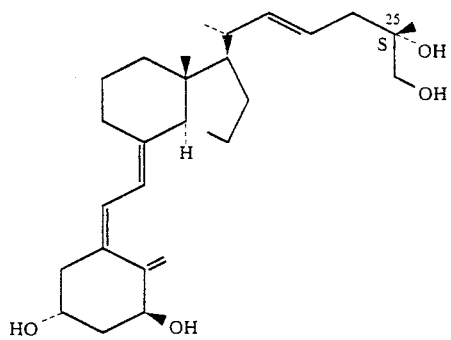
Ia and

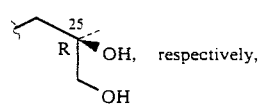
Ib, respectively, comprises the reaction of the corresponding epimer of the formula

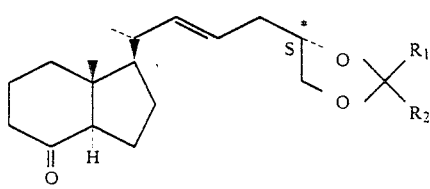
IIa or

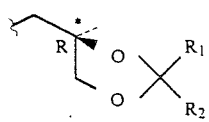
IIb wherein $R_1$ and $R_2$ are as previously described, with a compound of formula III to yield the corresponding epimer of the formula

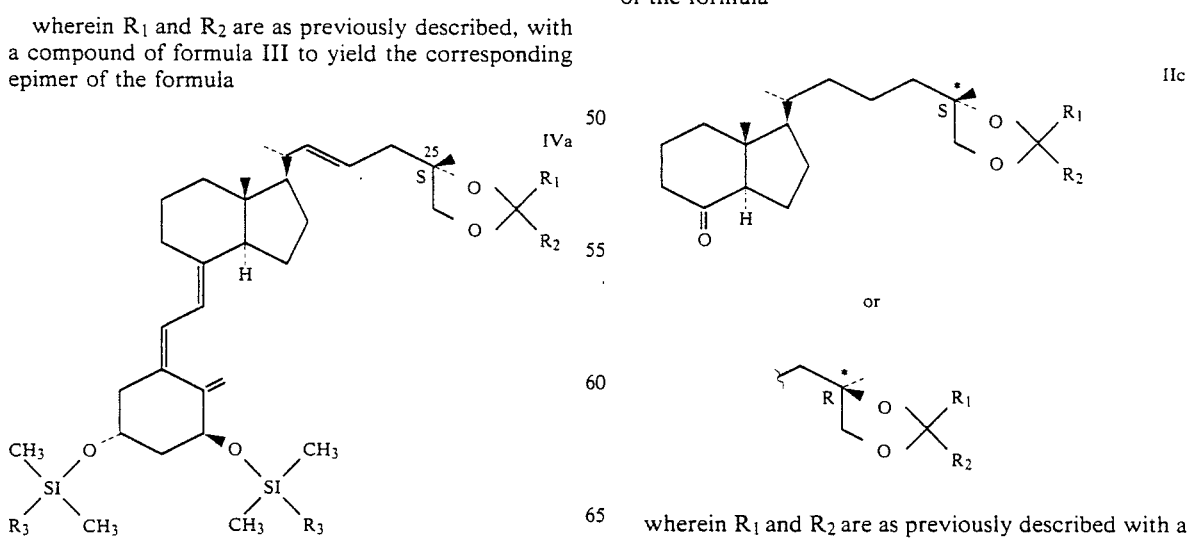
IVa or

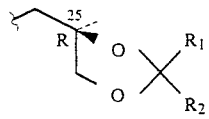
IVb

The compound of formula IVa or IVb is deprotected, that is, it si treated to remove the hydroxyl derivatizing groups. The reaction conditions for the foregoing conversions are the same as those previously described.

The preparation of the trihydroxycholecalciferols can be further illustrated as follows:

The process for the preparation of 1,25S,26-trihydroxycholecalciferol, and 1,25R,26-trihydroxycholecalciferol of formulas

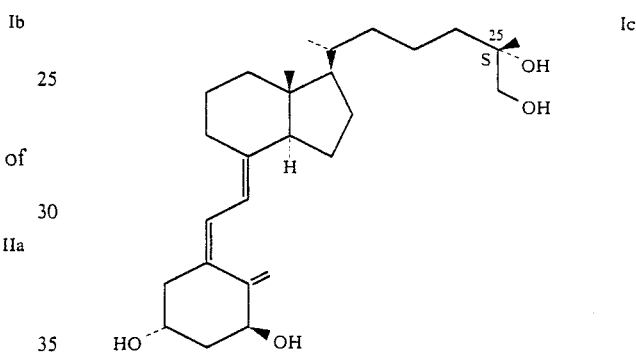
Ic and

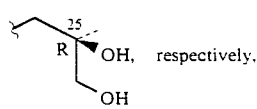
Id, respectively, comprises the reaction of the corresponding compound of the formula

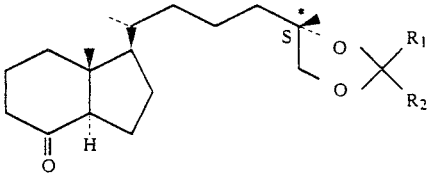
IIc or

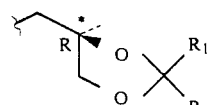

wherein $R_1$ and $R_2$ are as previously described with a compound of formula III to yield the corresponding compound of the formula

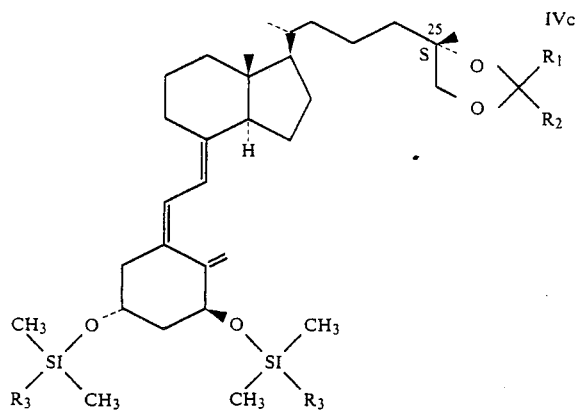

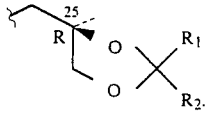

The compound of formula IVc or IVd is deprotected, that is, it is treated to remove the hydroxyl derivatizing groups. The reaction conditions for the foregoing conversions are the same as those previously described.

The starting materials of formulas IIa, IIb, IIc and IId can be prepared as set forth Formula Schemes I and II which follow.

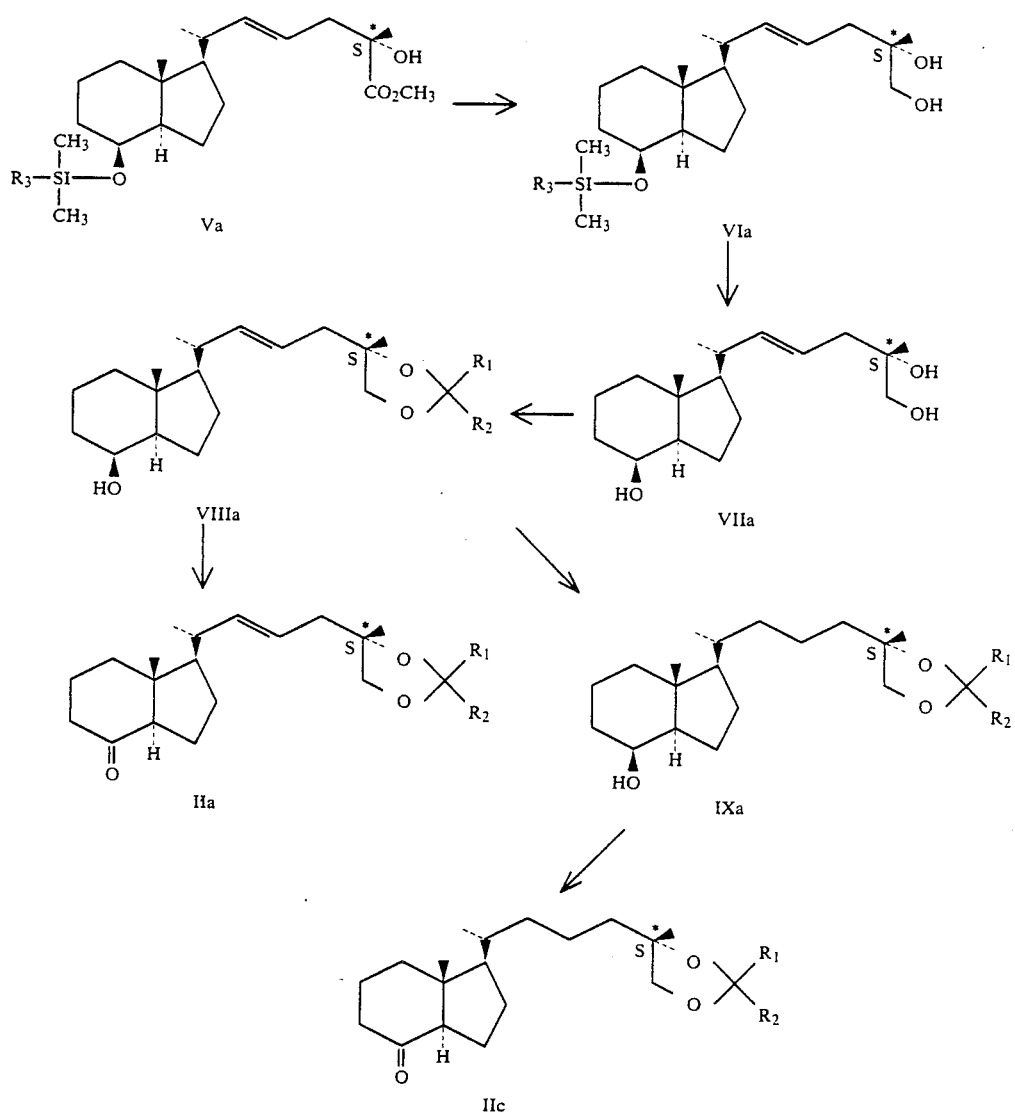

wherein $R_1$, $R_2$ and $R_3$ are as previously described.

Formula Scheme II

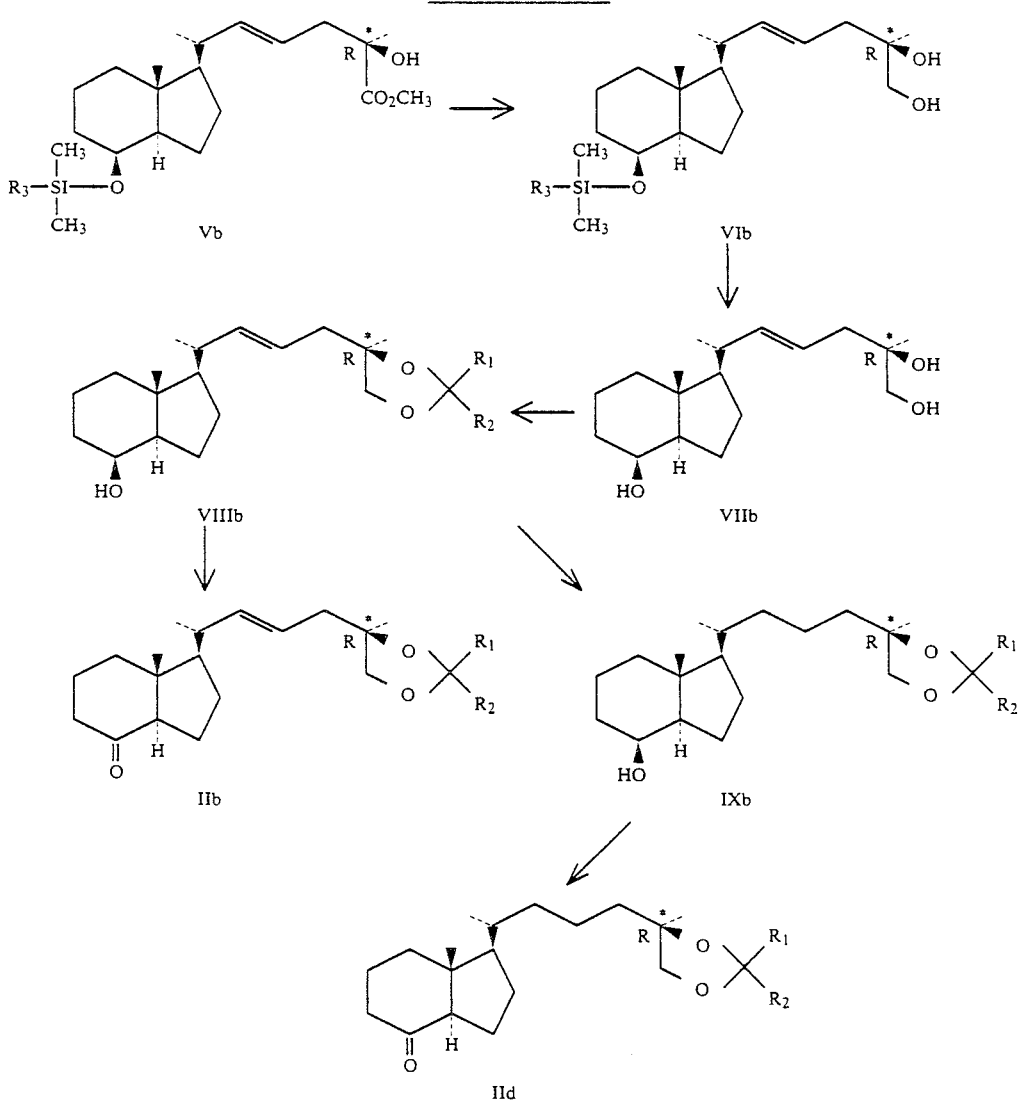

wherein $R_1$, $R_2$ and $R_3$ are as previously described.

In reaction Scheme I and II the compounds of formulas IIa, IIb, IIc and IId also form part of the invention and are prepared, respectively, from the known compounds of formulas Va and Vb. More specifically, a compound of formula Va or Vb is reduced with lithium aluminum hydride in an anhydrous conventional ether solvent, for example, a tetrahydrofuran solution at 0° C. to give the corresponding diol of formula VIa or VIb. Conversion of the corresponding compound VIa or VIb to the corresponding triol of formula VIIa or VIIb can be carried out by removal of the protecting groups, for example, tert.butyl-dimethylsilyl group, by 48% aqueous hydrogen fluoride in a mixture of acetonitrile and tetrahydrofuran. Protection of the vicinal diol of the side chain of a compound of formula VIIa or VIIb by conversion to the acetonide of the corresponding formula, VIIIa or VIIIb can be accomplished by treatment for example, with 2,2-dimethoxypropane and catalyzed, for example, with p-toluenesulfonic acid at room temperature. Conversion of the resulting compound of formula VIIIa or VIIIb to the dihydro analog of formula IXa or IXb can be achieved by hydrogenation over 10% palladium on carbon catalyst at atmospheric pressure in a solvent, for example, ethyl acetate and the like. Finally, the corresponding ketone of formula IIa or IIb and IIc or IId can be obtained by oxidation of a compound of formula VIIIa or VIIIb and IXa or IXb, respectively, for example, with 2,2'-bipyridinium chlorochromate in a solvent, for example, methylene chloride and in the presence of anhydrous sodium acetate.

The process of the preparation of 1α,25S,26-trihydroxyergocalciferol and 1α,25R,26-trihydroxyergocalciferol of the formulas, Ie

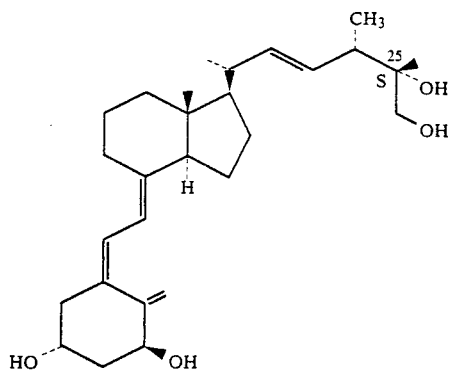

and

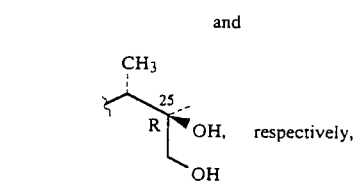

respectively, comprises the reaction of the corresponding epimer of the formulas IIe

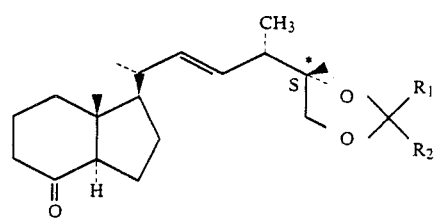

or

IIf

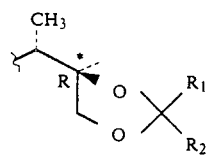

wherein $R_1$ and $R_2$ are as previously described, with a compound of formula III to yield the corresponding epimer of the formula IVe

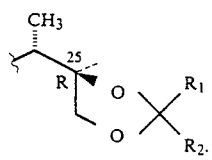

or

IVf

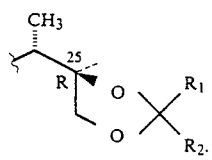

The compound of formula IVe or IVf is deprotected, that is, it is treated to remove the hydroxyl derivatizing groups. The reaction conditions for the foregoing conversions are the same as those previously described.

The starting material IIe can be prepared as set forth in Formula Scheme III.

Formula Scheme III

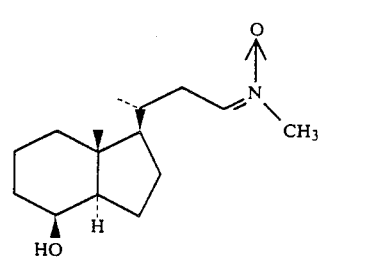

X

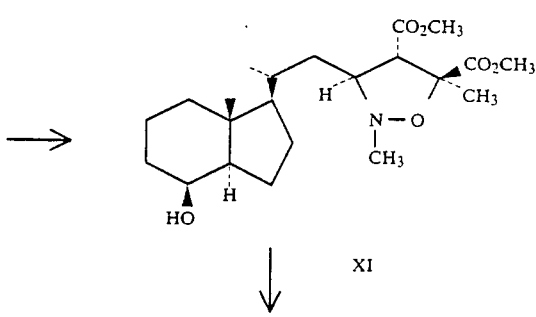

XI

-continued
Formula Scheme III

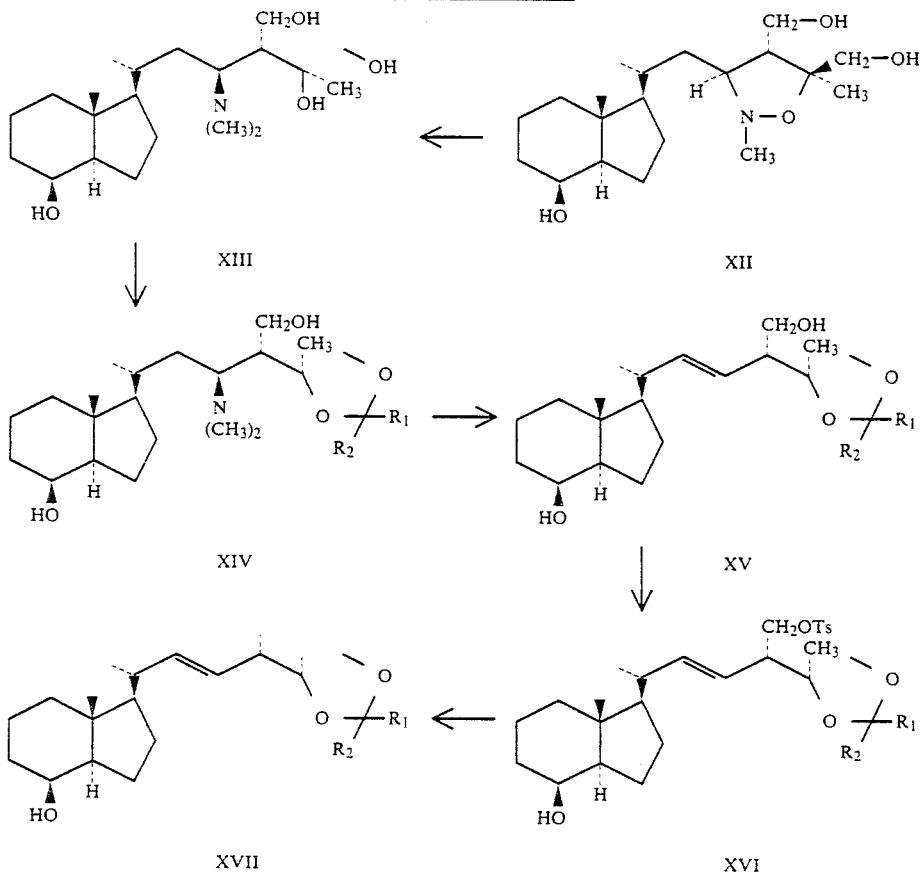

wherein $R_1$ and $R_2$ are as previously described, and Ts is

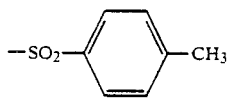

The starting material IIe can be prepared as set forth in Formula Scheme III from the known compound of formula X. The compound of formula X is heated with methyl mesaconate in an anhydrous conventional aromatic solvent, for example, an xylene solution at 140° C. to give the isoxazolidine diester of formula XI. Conversion of the compound of formula $XI_x$ to the corresponding diol of formula XII can be carried out by reduction with lithium aluminum hydride in an anhydrous conventional ether solvent, for example a tetrahydrofuran solution at an ice bath temperature. Opening of the isoxazolidine ring of the compound of formula XII to produce the compound of the formula XIII is carried out by sequence of N-methylation with methyliodide in toluene solution at 60° C. followed by reduction with zinc dust in acetic acid solution at room temperature. Alternatively, the last reduction can also be performed with lithium aluminum hydride in tetrahydrofuran solution. Protection of the vicinal diol of the side chain of the compound of formula XIII by conversion to the acetonide of formula XIV can be accomplished by treatment, for example, with 2,2-dimethoxypropane and catalyzed, for example, with p-toluenesulfonic acid at room temperature, to give the compound of formula XIV. Conversion of the compound of formula XIV to the compound of formula XV is carried out by methylation with methyliodide in dry toluene in the presence of potassium carbonate at 65° C., followed by elimination effected with potassium t-butylate at 55° C. and finally at 100° C. The compound of the formula XV is then converted to the tosylate of the formula XVI with p-toluenesulfonyl chloride in methylene chloride solution in the presence of triethylamine. Reduction of the compound of formula XVI to the compound of formula XVII is carried out with lithium aluminum hydride in tetrahydrofuran solution at the reflux temperature. Finally, the ketone of the formula IIe can be obtained by oxidation of the compound of formula XVII with, for example, 2,2'bipyridinium chlorochromate in a solvent, for example, methylene chloride in the presence of anhydrous sodium acetate.

The compounds of formula I have anti-proliferative and differentiation-inducing activity. The compounds of formula I are therefore useful as agents for the treatment of diffuse tumors such as leukemias, as exemplified by but not limited to monocytic and promyelocytic leukemias, as well as solid tumors, as exemplified by but not limited to lung carcinomas melanoma colorectal carcinoma, and breast tumors in warm-blooded animals. The anti-proliferative and differentration-inducing activity of the compounds of formula I can be demonstrated utilizing the procedure hereinafter described.

More particularly, in the test procedure, the tissue culture medium which can be used is RPMI-1640 supplemented prior to use to 10% v/v with fetal bovine serum (heat inactivated at 56° for 30 minutes), to 130 units per ml with penicillin and 130 μg per ml with streptomycin, and to an additional 1.6 millimolar with L-glutamine.

The test compounds are dissolved in sufficient ethanol to yield stock solutions of $1 \times 10^{-2}$ molar. Reduced lighting is employed when working with the compounds, and the stock solutions are stored in the dark at $-20°$ in an argon atmosphere. The compounds are diluted with tissue culture medium and added to flasks containing HL-60 cells to achieve the final concentrations described in each experiment.

The promyelocytic (HL-60) tumor cell line is maintained in liquid culture by serial weekly passage in tissue culture medium. In any experiment, three replicate flasks are incubated without compound (control) or in the presence of varying concentrations of compound. After 4 days of incubation at 37° in a humidified atmosphere of 5% carbon dioxide in air, cultures are evaluated for tumor cell proliferation, viability and differentiation.

Quantitation of Proliferation is done by enumerating the number of HL-60 cells in each individual flask (3 flasks per experimental point) using a model ZBI Coulter Counter. Results are shown as the number of cells per ml of tissue culture medium expressed as the mean ± standard deviation and as percent inhibition of proliferation calculated according to formula:

$$\left(1 - \frac{\text{mean number of cells in experimental cultures}}{\text{mean number of cells in control culture}}\right) \times 100$$

Viability of tumor cells is determined by the method of trypan blue dye exclusion. The cells in tissue culture medium are added to a four-fold larger volume of 0.4% trypan blue in saline. Cells are scored as viable upon microscopic examination if they exclude dye and as dead if they are stained blue. The viability of cells from all cultures described is never less than 94% clearly indicating that the compounds tested are not toxic to HL-60 cells in the concentrations employed.

Quantitation of differentiated cells is done by the biochemical method of nitroblue tetrazolium (NBT) reduction. Sufficient cells are pooled from replicate cultures, centrifuged at $220 \times g$, washed once with serum-free tissue culture medium, and resuspended to $1 \times 10^6$ cells per ml in $Ca^{++}$−deficient phosphate buffered saline (prepared by supplementing $Ca^{++}$−$Mg^{++}$-free phosphate buffered saline (PBS) to 10% v/v with heat-inactivated fetal bovine serum). Nitroblue tetrazolium is dissolved at 1 mg per ml in $Ca^{++}$−$Mg^{++}$-deficient PBS with gentle heating and mixing. Tetradecanoyl phorbol acetate (TPA) is dissolved at 1 mg per ml in ethanol and stored at $-20°C$. Just prior to use, a working solution of TPA is prepared by diluting the stock concentration 100-fold with $Ca^{++}$−$Mg^{++}$-deficient PBS. The test is done in $12 \times 75$ mm tubes by adding 0.5 ml $Ca^{++}$−deficient PBS, 1.0 ml of HL-60 cells, 0.5 ml of NBT solution, and 0.02 ml of the working TPA solution. After mixing, the tubes are incubated in a 37° water bath for 25 minutes then transferred to ice. Undifferentiated and differentiated cells present in any sample are determined microscopically by surveying 200–400 cells per sample. Cells without pigmented granules (clear cells) are judged to be undifferentiated while those containing greater than 3 blue-black formazan granules are scored as differentiated. Generally, differentiated cells are intensely pigmented clearly indicating the enzymatic conversion of NBT to formazan. Results are expressed as the percentage of differentiated cells present in any sample as calculated according to the formula:

$$100 \times \frac{\text{number of formazan positive cells}}{\text{total number of cells counted}}$$

The results obtained with representative compounds of the invention are set out in Tables I, II, III and IV.

TABLE I

Ethanol, employed as vehicle, does not inhibit proliferation or induce differentiation of HL-60 cells, in vitro:

| Expt. number | Compound and concentrated | Proliferation[a] HL-60 cells per ml $\times 10^{-4}$ (mean ± SD) | Differentiation formazan "+" cells total cells counted | % "+" |
|---|---|---|---|---|
| I | None (control) | 140.0 ± 9.3 | 6/337 | 2 |
|  | Ethanol (0.18%, v/v) | 146.0 ± 14.1 | 4/330 | 1 |
| II | None (control) | 28.2 ± 0.6 | 1/325 | <1 |
|  | Ethanol (0.01%, v/v) | 28.9 ± 1.4 | 2/371 | <1 |
| III | None (control) | 25.5 ± 2.3 | 3/452 | <1 |
|  | Ethanol (0.01%, v/v) | 26.5 ± 1.2 | 2/427 | <1 |

[a]The initial HL-60 cell densities employed in these experiments were: in experiment I, $5 \times 10^4$ per ml, and in experiments II and III, $1 \times 10^4$ per ml.

TABLE II

Anti-proliferation and differenetiation-inducing effects of $1\alpha,25S,26\text{-}(OH)_3D_3^{(1)}$; $1\alpha,25R,26\text{-}(OH)_3D_3^{(2)}$, $1\alpha,25S,26\text{-}(OH)_3\Delta^{22}D_3^{(3)}$; and $1\alpha,25S,26\text{-}(OH)_3D_2^{(4)}$, at doses of 1 to $10 \times 10^{-9}$ molar on HL-60 cells, in vitro

| Compound and[a] concentration ($\times 10^{-9}$ molar) | Proliferation[b] HL-60 cells per ml $\times 10^{-4}$ (mean ± SD) | inhibition of proliferation (%) | Differentiation formazan "+" cells total cells counted | % "+" |
|---|---|---|---|---|
| Control (no drug) | 54.0 ± 1.8 | — | 13/345 | 4 |

TABLE II-continued

Anti-proliferation and differenetiation-inducing effects of
1α,25S,26-(OH)₃D₃[1]; 1α,25R,26-(OH)₃D₃[2],
1α,25S,26-(OH)₃Δ²²D₃[3]; and 1α,25S,26-(OH)₃D₂[4], at doses of 1 to
10 × 10⁻⁹ molar on HL-60 cells, in vitro

| Compound and[a] concentration ($\times 10^{-9}$ molar) | | HL-60 cells per ml $\times 10^{-4}$ (mean ± SD) | inhibition of proliferation (%) | Differentiation formazan "+" cells total cells counted | % "+" |
|---|---|---|---|---|---|
| 1α,25S,26-(OH)₃D₃ | 1 | 48.0 ± 3.4 | 11 | 19/293 | 7 |
| " | 3 | 50.7 ± 1.9 | 6 | 14/340 | 4 |
| " | 10 | 45.3 ± 1.0 | 16 | 142/349 | 41 |
| 1α,25R,26-(OH)₃D₃ | 1 | 50.9 ± 3.8 | 6 | 11/309 | 4 |
| " | 3 | 50.6 ± 1.2 | 7 | 22/315 | 7 |
| " | 10 | 43.2 ± 0.8 | 20 | 138/307 | 45 |
| 1α,25S,26-(OH)₃-Δ²²-D₃ | 1 | 50.7 ± 3.0 | 7 | 12/280 | 4 |
| " | 3 | 49.6 ± 0.8 | 8 | 50/366 | 14 |
| " | 10 | 32.3 ± 0.8 | 40 | 223/347 | 65 |
| None (medium control) | | 86.8 ± 7.2 | — | 3/311 | 1 |
| 1α,25S,26-(OH)₃-D₂ | 1 | 75.9 ± 1.4 | 12 | 4/302 | 1 |
| | 10 | 48.0 ± 1.7 | 44 | 97/300 | 32 |
| | 100 | 22.4 ± 0.1 | 74 | 306/311 | 98 |

[1] 1α,25S,26-trihydroxycholecalciferol.
[2] 1α,25R,26-trihydroxycholecalciferol.
[3] 1α,25S,26-trihydroxy-Δ²²-cholcalciferol.
[4] 1α,25S,26-trihydroxyergocalciferol.
[a] The vehicle (ethanol) concentration used in this experiment ranged from 0.000001% to 0.01% v/v.
[b] The HL-60 cell density at the initiation of these experiments was 1 × 10⁴ per ml, except for 1α,25S,26-(OH)₃-D₂ which had an initial cell density of 2 × 10⁴ cells per ml.

TABLE III

Anti-proliferation and differenetiation-inducing effects of
1α,25S,26-(OH)₃D₃; 1α,25R,26-(OH)₃D₃; and
1α,25S,26-(OH)₃Δ²²D₃ at doses of 10 to 1000 ×
10⁻⁹ molar on HL-60 cells, in vitro

| Compound and[a] concentration ($\times 10^{-9}$ molar) | | HL-60 cells per ml $\times 10^{-4}$ (mean ± SD) | inhibition of proliferation (%) | Differentiation formazan "+" cells total cells counted | % "+" |
|---|---|---|---|---|---|
| Control (no drug) | | 32.0 ± 1.3 | — | 3/317 | 1 |
| 1α,25S,26-(OH)₃D₃ | 10 | 27.2 ± 1.9 | 15 | 81/383 | 21 |
| " | 30 | 14.5 ± 0.8 | 55 | 365/425 | 86 |
| " | 100 | 10.7 ± 0.8 | 67 | 271/274 | 99 |
| " | 1000 | 8.3 ± 0.5 | 74 | 342/344 | 99 |
| 1α,25R,26-(OH)₃D₃ | 10 | 25.9 ± 1.8 | 19 | 113/336 | 34 |
| " | 30 | 13.6 ± 0.7 | 58 | 296/332 | 90 |
| " | 100 | 9.2 ± 0.3 | 71 | 350/355 | 98 |
| " | 1000 | 7.8 ± 0.2 | 76 | 365/367 | 99 |
| 1α,25S,26-(OH)₃-Δ²²-D₃ | 10 | 19.3 ± 9.5 | 40 | 229/379 | 60 |
| " | 30 | 10.6 ± 0.5 | 67 | 286/297 | 96 |
| " | 100 | 8.8 ± 0.3 | 73 | 378/381 | 99 |
| " | 1000 | 7.2 ± 0.3 | 78 | 299/302 | 99 |

[a] The vehicle (ethanol) concentration used in this experiment ranged from 0.0001 to 0.01%, v/v.
[b] The HL-60 cell density at the initiation of this experiment was 1 × 10⁴ per ml.

TABLE IV

Anti-proliferation and differenetiation-inducing effects of
1α,25S,26-(OH)₃D₃; 1α,25R,26-(OH)₃D₃; and
1α,25S,26-(OH)₃Δ²²D₃ at doses of 3 to 100 ×
10⁻⁹ molar on HL-60 cells, in vitro

| Compound and[a] concentration ($\times 10^{-9}$ molar) | | HL-60 cells per ml $\times 10^{-4}$ (mean ± SD) | inhibition of proliferation (%) | Differentiation formazan "+" cells total cells counted | % "+" |
|---|---|---|---|---|---|
| None (vehicle at 0.01%, v/v) | | 26.6 ± 1.0 | — | 4/447 | 1 |
| 1α,25S,26-(OH)₃D₃ | 3 | 28.3 ± 0.5 | 0 | 5/449 | 1 |
| " | 10 | 23.7 ± 1.0 | 11 | 69/473 | 15 |
| " | 30 | 20.7 ± 1.0 | 22 | 244/422 | 58 |
| " | 100 | 18.1 ± 0.9 | 32 | 337/415 | 81 |
| 1α,25R,26-(OH)₃D₃ | 3 | 26.7 ± 2.0 | 0 | 5/425 | 1 |
| " | 10 | 25.3 ± 0.6 | 5 | 86/454 | 19 |
| " | 30 | 21.1 ± 0.6 | 21 | 314/490 | 64 |
| " | 100 | 16.5 ± 0.4 | 38 | 372/422 | 84 |
| 1α,25S,26-(OH)₃-Δ²²-D₃ | 3 | 24.9 ± 1.2 | 6 | 14/476 | 3 |

TABLE IV-continued

Anti-proliferation and differenetiation-inducing effects of
$1\alpha,25S,26\text{-}(OH)_3D_3$; $1\alpha,25R,26\text{-}(OH)_3D_3$; and
$1\alpha,25S,26\text{-}(OH)_3\Delta^{22}D_3$ at doses of 3 to 100 ×
$10^{-9}$ molar on HL-60 cells, in vitro

| Compound and[a] concentration ($\times 10^{-9}$ molar) | | Proliferation[b] | | Differentiation | |
|---|---|---|---|---|---|
| | | HL-60 cells per ml $\times 10^{-4}$ (mean ± SD) | inhibition of proliferation (%) | formazan "+" cells total cells counted | % "+" |
| " | 10 | 22.0 ± 0.6 | 17 | 198/607 | 33 |
| " | 30 | 18.5 ± 0.7 | 30 | 319/456 | 70 |
| " | 100 | 16.9 ± 0.7 | 36 | 350/409 | 86 |

[a]In this experiment, vehicle (ethanol) concentration was held constant at 0.01%, v/v.
[b]The HL-60 cell density at the initiation of this experiment was $1 \times 10^4$ per ml.

The test data which follows includes the experimental methodology and procedures to determine cell proliferation viability and cellular differentiation by nitrobluetetrazolium reduction earlier described and includes a functional evaluation of cellular differentiation.

Quantitation of differentiated HL-60 cells on a functional basis was done by enumerating the number of cells in any sample which had acquired the ability to phagocytose (bind/internalize) particulate material from their environment, a characteristic of mature granulocytes. Sufficient cells were pooled from replicate cultures, centrifuged at 220 xg, washed once with serum-free tissue culture medium, and resuspended to $1 \times 10^6$ cells per ml. in serum-free tissue culture medium. To a 1.0 ml. sample in 12×75 mm. tubes was added 0.1 ml of a 1:10 dilution from stock of fluorescent microspheres. Cells and particle were mixed incubated for 15 minutes in a 37° water bath, collected in a transfer pipet, and overlayed onto a 5 ml. cushion of fetal bovine serum in a 15 ml. conical culture tube. After centrifugation at 150×g. for 8 minutes, the excess particulate (upper layer) was discarded as was the remainder of the serum cushion leaving only a cell pellet and cell-associated particulate. The resultant pellets were resuspended in 1.0 ml. of tissue culture medium containing 10% fetal bovine serum, transferred to a hemacytometer, and evaluated microscopically using both ultraviolet and visible light sources. Undifferentiated and differentiated cells present in any sample were determined microscopically by surveying 200–400 cells per sample. Non-fluorescent cells, identified only by visible light, were judged to be undifferentiated while those containing fluorescent particles were judged to be differentiated. Generally, differentiated cells were intensely fluorescent clearly indicating extensive phagocytosis of particulate material. Results are expressed as the percentage of differentiated cells present in any sample as calculated according to the formula:

$$100 \times \frac{\text{number of phagocytic cells}}{\text{total number of cells counted}}.$$

The results obtained with representative compounds of the invention are set out in Table V.

TABLE V

Anti-proliferation and differentiation-inducing effects of $1\alpha,25S,26\text{-}(OH)_3D_3$; $1\alpha,25R,26\text{-}(OH)_3D_3$; $1\alpha,25S,26\text{-}(OH)_3\text{-}\Delta^{22}\text{-}D_3$; and $1\alpha,25S,26\text{-}(OH)_3D_2$ at doses of 1 to 100 × $10^{-9}$ molar on HL-60 cells, in vitro.

| Compound and concentration ($\times 10^{-9}$ molar) | | Proliferation[c] | | Differentiation | | | |
|---|---|---|---|---|---|---|---|
| | | HL-60 cells per ml $\times 10^{-4}$ (mean ± SD) | inhibition of proliferation (%) | NBT reduction | | phagocytosis | |
| | | | | formazan "+" cells total cells counted | %"+" | phagocytic cells total cells counted | % "+" |
| Medium control (no drug) | | 68.5 ± 4.8 | — | 2/277 | <1 | 3/245 | 1 |
| Vehicle control[a] | | 66.3 ± 3.2 | 0 | 2/241 | <1 | 7/240 | 3 |
| $1\alpha,25S,26\text{-}(OH)_3D_3$ | 3 | 68.3 ± 4.0 | 0 | 12/278 | 4 | 13/267 | 5 |
| " | 10 | 70.0 ± 2.2 | 0 | 80/266 | 30 | 78/247 | 32 |
| " | 30 | 43.3 ± 3.9 | 35 | 191/244 | 80 | 196/264 | 74 |
| " | 100 | 29.3 ± 1.7 | 56 | 258/265 | 97 | 220/245 | 90 |
| $1\alpha,25R,26\text{-}(OH)_3D_3$ | 3 | 72.4 ± 0.8 | 0 | 30/342 | 9 | 31/285 | 11 |
| " | 10 | 59.9 ± 3.8 | 10 | 129/245 | 53 | 117/283 | 41 |
| " | 30 | 36.1 ± 1.7 | 46 | 226/258 | 88 | 190/243 | 78 |
| " | 100 | 27.8 ± 0.9 | 58 | 239/247 | 97 | 210/225 | 93 |
| $1\alpha,25S,26\text{-}(OH)_3\text{-}\Delta^{22}\text{-}D_3$ | 3 | 59.3 ± 1.6 | 11 | 78/272 | 29 | 71/281 | 25 |
| " | 10 | 50.4 ± 1.1 | 24 | 165/270 | 61 | 152/256 | 59 |
| " | 30 | 35.6 ± 1.6 | 46 | 228/257 | 89 | 214/256 | 84 |
| " | 100 | 28.9 ± 0.6 | 56 | 241/252 | 96 | 247/264 | 94 |
| None (medium control) | | 58.5 ± 1.8 | — | 2/317 | <1 | 2/278 | <1 |
| Vehicle (0.01% ethanol)[b] | | 58.0 ± 2.2 | 0 | 1/309 | <1 | 2/303 | <1 |
| $1\alpha 25S,26\text{-}(OH)_3\text{-}D_2$ | 1 | 60.3 ± 1.0 | 0 | 5/320 | 2 | 8/332 | 2 |
| " | 3 | 54.4 ± 1.1 | 7 | 20/310 | 7 | 18/334 | 5 |
| " | 10 | 42.0 ± 0.7 | 28 | 94/310 | 30 | 74/319 | 23 |
| " | 30 | 29.3 ± 1.1 | 50 | 176/308 | 57 | 188/360 | 52 |
| " | 100 | 20.8 ± 0.8 | 64 | 314/322 | 98 | 324/352 | 92 |

[a]All cultures (except medium controls) contained 0.001%, v/v, ethanol as vehicle.
[b]All cultures (except medium controls) contained 0.01%, v/v, ethanol as vehicle.
[c]The HL-60 cell density at the initiation of these experiments was $2 \times 10^4$ per ml.

The R and S epimers of formula I may be administered to a warm-blooded animal requiring treatment of tumor cells, including leukemias, in dosages that are in the range of 0.05 micrograms/kg to 500 micrograms/kg per day. It is to be understood, however that the dosages set forth herein are to be adjusted to individual requirements and, therefore, are exemplary only and that they do not, to any extent, limit the scope or practice of the invention. The referred to R or S epimer can be administered orally, but they can also be administered subcutaneously, intramuscularly, intravenously, or intraperitoneally.

More particularly, the R and S epimers of formula I can be administered utilizing formulation, for example compositions such as tablets, capsules, and the like, or elixirs for oral administration, or in sterile solutions or suspensions for parenteral administration. About 0.05 micrograms to 500 micrograms of an R or S epimer of formula I is compounded with a pharmaceutically acceptable vehicle, carrier, excipient, binder, preservative, stabilizer, flavor, and the like, in a unit dosage as called for by accepted pharmaceutical practice. The amount of active substance in the foregoing compositions or preparations is in the range previously indicated.

Illustrative of the adjuvants which may be incorporated into tablets capsules, and the like are the following: a binder such as gum tragacanth, acacia, corn starch, or gelatin; an excipient such as dicalcium phosphate; a disintegrating agent such as corn starch, potato starch, algenic acid, and the like; a lubricant such as magnesium sterate; a sweetening agent such as sucrose, lactose or saccharin; and a flavoring agent such as peppermint, oil of wintergreen, or cherry. Various other materials may be present as coatings or to otherwise modify the physical form of the dosage unit. For instance, tablets may be coated with shellac, sugar, or both. A syrup or elixir may contain the active compound, sucrose as a sweetening agent, methyl, and propyl parabens as preservatives, a dye, and a flavoring such as cherry or orange flavor.

Sterile compositions for injection can be formulated according to conventional pharmaceutical practice by dissolving or suspending the active substance in a vehicle, such as water for injection, a naturally-occurring vegetable oil, such as sesame oil, coconut oil, peanut oil, cottonseed oil, and the like, or a synthetic fatty vehicle such as ethyl oleate or the like. Buffers, preservatives, antioxidants and the like can be incorporated as required.

The Examples which follow further illustrate the invention. All temperatures are in degrees Centigrade unless otherwise stated.

EXAMPLE 1

Preparation of
[1R-[1R-R*,E,S*),3aα,4β,7aβ11-6-(octahydro-4-[(1, 1-dimethylethyl)-dimethylsilyl]-oxy-7a-methyl-1H-inden-1-yl) -2-methyl-4-heptene-1,2-diol To a cooled (0° C.) suspension of 0.122 g of lithium aluminum hydride and 3.2 ml of dry tetrahydrofuran was added 0.336 g of [1R-[1β-(R*,E,S*),3aα,4β,7aβ]]-6-(octahydro-4-[(1, 1-dimethylethyl)dimethylsilyl]oxy-7a-methyl-1H-inden-1-yl) -2-hydroxy-2-methyl-4-heptenecarboxylic acid methyl ester and 4 ml of dry tetrahydrofuran over 2 minutes. After one hour, 0.061 g of lithium aluminum hydride was added, the mixture stirred for 20 minutes then the cooling bath was removed. After an additional 2.5 hours, the mixture was recooled to OOC, 0.6 ml of ethyl acetate was added. After stirring for 10 minutes, 3.5 ml of saturated ammonium chloride solution was added, cooling bath removed and the mixture stirred for 25 minutes, and then filtered through Celite washing with chloroform and ethyl acetate. The filtrates were dried over anhydrous sodium sulfate, filtered and concentrated under reduced pressure. The residue was chromatographed on silica gel (hexane-ethyl acetate, 6:4) to give [1R-[1,β-(R*E,S*),3aα,4β,7aβ]]-6-(octahydro-4-[(1,1-dimethylethyl)-dimethylsilyl]-oxy-7a -methyl-1H-indenyl)-2-methyl-4-heptene-1,2-diolin 89% yield, $[\alpha]_D^{25}$ 48.75° (c 0.9388.Chloroform).

EXAMPLE 2

Preparation [1R-[1β-(R*,E,S*),3aα,4β,7aβ 11-6(octahydro-4-hydroxy-7a-methyl-1H-inden-1-yl) -2-methyl-4-heptene-1,2-diol To a solution of 0.257 g of [1R-[1β-(R*,E,S*),3aα, 4β,7aβ]]-6-(octahydro-4-[1,1-dimethylethyl)-dimethylsilyl]-oxy-7a-methyl-1H-inden-1-yl)-2-methyl-4-heptene-1,2-diol, 3.6 ml of acetonitrile and 3.0 ml of tetrahydrofuran under argon Was added 2.8 ml of 48% aqueous hydrogen fluoride. The cloudy mixture was stirred for 3 hours, then poured into 200 ml of chloroform and 20 ml of water. The aqueous phase was extracted 2×100 ml of chloroform and the combined chloroform layers were washed 1×20 ml of saturated sodium bicarbonate. The extract was dried over anhydrous sodium sulfate filtered and concentrated in vacuo. The residue was chromatographed (ethyl acetate) on silica gel to give 0.176 g (95%) of [1R-[1β-(R*,E,S*). 3aα,4β,7aβ]]-6-(octahydro-4-hydroxy-7a-methyl-1H-inden-1-yl) -2-methyl-4-heptene-1,2-diol, m.p. 87°-88° (methanol-water, 1:1), $[\alpha]_D^{25}$ +28.2° (c 0.748, chloroform).

EXAMPLE 3

Preparation of
[1R-[1β-(R*,E,S*),3aα,4β,7aβ]]-octahydro-7a-methyl-1-[1-methyl-4-[(2,2,4-trimethyl 1.3-dioxolan-4-yl)-4-butenyl]-1H-inden-4-ol A solution of 0.254 g of [1R-[1,β(R*,E,S*),3a α, 4β,7aβ]]-6-(octahydro-4-hydroxy-7a-methyl-1H-inden-1-yl) -2-methyl-4-heptene-1,2-diol, 10 ml of 2,2-dimethoxypropane and 16 mg of p-toluenesulfonic acid monohydrate was stirred under argon at room temperature for 50 minutes, then 2 ml of methanol was added. The mixture was stirred an additional 45 minutes, then 2.5 ml of saturated sodium bicarbonate solution was added. The mixture was stirred for 1 hour, then diluted with 150 ml of chloroform and washed 1×10 ml of water. The aqueous phase was extracted 2×50 ml of chloroform and the combined chloroform layers dried over anhydrous sodium sulfate. The mixture was filtered, concentrated under reduced pressure, and chromatographed on silica gel (hexane-ethyl acetate, 25:75) to give 0.259 (90%) of [1R-[1β-(R*,E,S*),3aα,4β,7aβ]]-octahydro-7a-methyl-1-[1-methyl-4-[(2,2,4-trimethyl 1 3-dioxolan-4-yl)-4-butenyl]-1H-inden-4-ol as an oil; $[\alpha]_D^{25}$ +21.27° (c o.6018, chloroform).

EXAMPLE 4

Preparation of
[1R-[1β(R*,S*),3aα,4β,7aβ]]-octahydro-7a-methyl-1-[1-methyl-4-(2,2,4-trimethyl-1,3-dioxolan-4-yl)butyl]-1H-inden-4-ol

[1R-[1β-(R*,E,S*),3aα,4β,7aβ]]-Octahydro-7a-methyl-1-[1-methyl-4-[(2,2,4-trimethyl-1,3-dioxolan-4-yl) -4-butenyl]-1H-inden-4-ol was hydrogenated at atmospheric pressure over 10% palladium on carbon in ethyl acetate. Filtration and removal of solvent in vacuo gave quantitatively amorphous [1R-[1β(R*,S*),3aα,4β,7aβ]]-octahydro-7a-methyl-1-[1-methyl-4-(2,2,4-trimethyl-1,3-dioxolan-4-yl)butyl]-1H-inden-4-ol, $[\alpha]_D^{25} +33.3°$ (c 0.941, chloroform).

EXAMPLE 5

Preparation of
[1R-(1R*,S*)-1β,3aα,7aβ]-octahydro-7a-methyl-1-]1-methyl-4-(2,2,4-trimethyl-1,3-dioxolan-4-yl)butyl]-4H-inden-4-one To a suspension of 1.720 g of 2,2'-bipyridinium chlorochromate and 0.860 g of anhydrous sodium acetate in 10 ml of methylene chloride, was added a solution of 0.500 g of [1R-[1β(R*,S*),3aα,4β,7aβ]]-octahydro-7a-methyl-1-[1-methyl-4-(2,2,4-trimethyl-1,3-dioxolan-4-yl) butyl]-1H-inden-4-ol in 5 ml of methylene chloride and the mixture obtained stirred at room temperature for 2 hours. Additional 0.800 g of 2,2'-bipyridinium chlorochromate was then added and the stirring continued for an additional 2.5 hours. After this time, 1 ml of 2-propanol was introduced and 15 minutes later, the mixture diluted with water and extracted with ether. The combined organic phases were dried, evaporated and the residue purified by fast filtration through silica (eluent: hexane-ethyl acetate, 3:1) to give 0.446 g (90% yield) of pure [1R-(1R*,S*)-1β,3aα,7aβ]-octahydro-7a-methyl-1-[1-methyl-4-(2,2,4-trimethyl-1,3-dioxolan-4-yl)-butyl]-4H-inden-4-one.

EXAMPLE 6

Preparation of
[1R-(1R*,2R,S*),1β,3aα,7aβ]-octahydro7a-methyl-1-[1-methyl-4-(2,2,4-trimethyl-1,3-dioxolan-4-yl)2-butenyl]-4H-inden-4-one A solution of 0.145 g of [1R-(1R*,2E,S*),1β,3aα,7aβ]-octahydro-7a-methyl-1-[1-methyl-4-(2,2,4-trimethyl-1,3-dioxolan-4-yl) -2-butenyl]-4H-inden-4-ol in 9 ml of dry methylene chloride was treated with 0.250 g of anhydrous sodium acetate and 0 500 g of 2,2'-bipyridinium chlorochromate and the mixture stirred at room temperature for two hours. After this time, an additional 0.250 g of 2,2'-bipyridinium chlorochromate was added and the stirring continued for two more hours. After this time, 0.5 ml of isopropyl alcohol was added and the mixture stirred for 15 minutes, then diluted with water, and extracted with 3×50 ml of ether. The combined organic phases were washed with water, dried and evaporated to dryness. The crude residue obtained was purified by chromatography on silica gel eluting with hexane-ethyl acetate (3:1) to give 0.134 g (93%) of pure [1R-(1R*,2E,S*),1β,3aα,7aβ]-octahydro-7a-methyl-1-[1-methyl-4-(2, 2,4-trimethyl-1,3-dioxolan-4-yl)-2-butenyl]-4H-inden-4-one, $[\alpha]_D^{25}$ (c 0.2, ethanol).

EXAMPLE 7

Preparation of 1α,25S,26-trihydroxycholecalciferol 1,3-dimethyl-t-butylsilyl 25,26-acetonide A solution of 1.430 g of [3S-(3α,5β,Z)]-2-[2-methylene-3,5 bis-[(1,1-dimethylethyl)dimethylsilyloxy]cyclohexylidene]ethyldiphenylphosphine oxide in 30 ml of anhydrous tetrahydrofuran was treated dropwise and under argon at −78° C. with 1.4 ml of a 1.7 molar solution of n-butyllithium in hexane. Five minutes after the addition was completed a solution of 0.460 g of [1R-(1R*,S*)-1β,3aα,7aβ]-octahydro-7a-methyl-1-[1-methyl-4-(2,2,4-trimethyl-1,3-dioxolan-4-yl) -butyl]-4H-inden-4-one in 5 ml of anhydrous tetrahydrofuran was added dropwise and the resulting mixture stirred at −78° C. 2.5 hours. It was then treated at −78° C. with 5 ml of a 1N aqueous solution of sodium bicarbonate and potassium-sodium tartrate, allowed to come to room temperature and extracted with ethyl acetate. The combined organic extracts were dried, evaporated and the residue purified by chromatography on silica (using hexane-ethyl acetate, 5:1 as eluent) to give 0.91 g (95%) of pure 1α,25S,26-trihydroxycholecalciferol 1,3-dimethyl-t-butylsilyl 25,26-acetonide.

EXAMPLE 8

Preparation of 1α,25S,26-trihydroxycholecalciferol

To a solution of 0.91 g of 1α,25S,26-trihydroxycholecalciferol 1,3-dimethyl-t-butylsilyl 25,26-acetonide in 200 ml of methanol 45 g of a cation exchange resin (AG 50W-X4, 200–400 mesh from Bio-Rad Laboratory. Prewashed with methanol) was added and the mixture stirred at room temperature under argon for 16 hours. After filtration, the methanol solution was evaporated to dryness and the residue redissolved in 100 ml of ethyl acetate and washed 3x with brine. The organic phases were combined, dried evaporated and the residue purified by chromatography on silica (eluted with ethyl acetate) to give 0.486 g (86% yield) of pure 1α,25S,26-trihydroxycholecalciferol, m.p. 163°–164°, $[\alpha]_D^{25} +58.8°$ (c 0.5, methanol).

EXAMPLE 9

Preparation of
1α,25S,26-trihydroxy-Δ$^{22}$-cholecalciferol

A solution of 0.354 g of [3S-(3α,5β,Z)]-2-[2-methylene-3,5-bis-[(1,1-dimethylethyl)dimethylsilyloxy]cyclohexylidene]ethyldiphenylphospine oxide in 8 ml of dry tetrahydrofuran was cooled at −78° C. and treated dropwise under argon with 0.370 ml of a 1.6 molar solution of n-butyllithium in hexane.

After stirring for 5 minutes a solution of 0.113 g of [1R-(1R*,2E,S*),1β,3a α,7aβ]octahydro-7a-methyl-1-[1-methyl-4-(2, 2,4-trimethyl-1,3-dioxolan-4-yl)-2-butenyl]-4H-inden-4-one in 2 ml of dry tetrahydrofuran was slowly added and the resulting mixture stirred at −78° C. for two hours. It was then treated with 5 ml of a 1:1 mixture of 1N sodium bicarbonate and 1N potassium sodium tartrate, allowed to come to room temperature, diluted with water and extracted with 3×75 ml of ethyl acetate. The combined organic extracts were washed with brine, dried and evaporated. The residue was purified by chromatography on silica gel, eluting with hexane-ethyl acetate (9:1) to give 0.220 g of a colorless thick oil. This was dissolved in 25 ml of methanol, treated with 3.5 g of a cation exchange resin [AG 50W-X4, 200-400 mesh, Bio-Rad Laboratories] and stirred overnight. After filtration and washing of the resin with 20 ml of methanol, the solvent was evaporated in vacuo and the residue dissolved in ethyl acetate and washed with 2×30 ml of 2N sodium bicarbonate solution, followed by 3×30 ml of brine. The residue obtained after evaporation of solvent was purified by chromatography on silica gel, eluting with ethyl acetate to give 0.131 g (90%) of pure 1α,25S,26-trihydroxy-$\Delta^{22}$-cholecalciferol as a white, amorphous powder; $[\alpha]_D^{25}$ +44.9 (c 0.2, ethanol).

EXAMPLE 10

| Injectable Dosage Form Formulation | |
|---|---|
| Ingredient | Amount/ml |
| Sodium Chloride | 1.5 mg |
| Sodium Phosphate, Monobasic | 9.2 mg |
| Disodium Edetate | 1.0 mg |
| Isoascorbic Acid (D) | 10.0 mg |
| Tween 20[(1)] | 4.0 mg |
| 1α, 25S,26-(OH)$_3$-$\Delta^{22}$-D$_3$ | At desired concentration |
| Sodium Hydroxide | q.s. pH 7.0 |
| Water for Injection | q.s. ad |

Method of Preparation
1) Dissolve sodium chloride, sodium phosphate, disodium edetate and isoascorbic acid in watr for injection (80% final volume).
2) In a separate container, dissolve the 1 α,25S,26-(OH)$_3$-$\Delta^{22}$-D$_3$ in Tween 20 heated to 60° C. Allow to cool to room temperature (<30° C.).
3) Combine the two solutions and adjust pH to 7.0 with 10% (w/v) sodium hydroxide solution.
4) Bring to final volume with water for injection.
5) Aseptically filter and fill this solution.
*Note all processing steps are conducted under nitrogen overlay*
(1) Polyoxyalkylene derivative of hexitol anhydride partial long chain fatty acid esters - Sp. pg. 1.08-1.13.

EXAMPLE 11

| Injectable Dosage Form Formulation | |
|---|---|
| Ingredient | Amount/ml |
| Sodium Chloride | 1.5 mg |
| Sodium Phosphate, Monobasic | 9.2 mg |
| Disodium Edetate | 1.0 mg |
| Isoascorbic Acid (D) | 10.0 mg |
| Tween 20 | 4.0 mg |
| 1α,25S.26-(OH)$_3$-D$_3$ | At desired concentration |
| Sodium Hydroxide | q.s. pH 7.0 |
| Water for Injection | q.s. ad |

Method of Preparation
1) Dissolve sodium chloride, sodium phosphate, disodium edetate and isoascorbic acid in water for injection (80% final volume).
2) In a separate container, dissolve the 1 α,25S,26-(OH)$_3$-D$_3$ in Tween 20 heated to 60° C. Allow to cool to room temperature (<30° C.).
3) Combine the two solutions and adjust pH to 7.0 with 10% (w/v) sodium hydroxide solution.
4) Bring to final volume with water for injection.
5) Aseptically filter and fill this solution.
*Note all processing steps are conducted under nitrogen overlay*

EXAMPLE 12

| Injectable Dosage Form Formulation | |
|---|---|
| Ingredient | Amount/ml |
| Sodium Chloride | 1.5 mg |
| Sodium Phosphate, Monobasic | 9.2 mg |
| Disodium Edetate | 1.0 mg |
| Isoascorbic Acid (D) | 10.0 mg |
| Tween 20 | 4.0 mg |
| 1α,25R,26-(OH)$_3$-D$_3$ | At desired concentration |
| Sodium Hydroxide | q.s. pH 7.0 |
| Water for Injection | q.s. ad |

Method of Preparation
1) Dissolve sodium chloride, sodium phosphate, disodium edetate and isoascorbic acid in water for injection (80% final volume).
2) In a separate container, dissolve the 1 α,25R,26-(OH)$_3$-D$_3$ in Tween 20 heated to 60° C. Allow to cool to room temperature (<30° C.).
3) Combine the two solutions and adjust pH to 7.0 with 10% (w/v) sodium hydroxide solution.
4) Bring to final volume with water for injection.
5) Aseptically filter and fill this solution.
*Note all processing steps are conducted under nitrogen overlay*

EXAMPLE 13

| Oral Dose Form Formulation | |
|---|---|
| | mg/capsule |
| 1 α,25S,26-(OH)$_3$-$\Delta^{22}$-D$_3$ | At desired concentration |
| Neobee M5[(1)] | 200.00 |
| Butylated Hydroxyanisole (BHA) | 0.01 |
| Butylated Hydroxytoluene (BHT) | 0.01 |

Method of Preparation
1) Dissolve 1 α,25S,26-(OH)$_3$-$\Delta^{22}$-D$_3$, BHA and BHT in Neobee M5 under a blanket of nitrogen.
2) Encapsulate.
(1) Medium chain tri-glycerides

EXAMPLE 14

| Oral Dose Form Formulation | |
|---|---|
| | mg/capsule |
| 1 α,25S,26-(OH)$_3$D$_3$ | At desired concentration |
| Neobee M5 | 200.00 |
| Butylated Hydroxyanisole | 0.01 |
| Butylated Hydroxytoluene | 0.01 |

Method of Preparation
1) Dissolve 1 α,25S,26-(OH)$_3$-D$_3$, BHA and BHT in Neobee M5 under a blanket of nitrogen.
2) Encapsulate.

EXAMPLE 15

| Oral Dose Form Formulation | |
|---|---|
| | mg/capsule |
| 1 α,25R,26-(OH)$_3$-D$_3$ | At desired concentration |
| Neobee M5 | 200.00 |
| Butylated Hydroxyanisole | 0.01 |
| Butylated Hydroxytoluene | 0.01 |

Method of Preparation
1) Dissolve 1 α,25R,26-(OH)$_3$-D$_3$, BHA and BHT in Neobee M5 under a blanket of nitrogen.
2) Encapsulate.

EXAMPLE 16

Preparation of [3S,4S,5S[3β,4α,5β[(2R*),1R*(1β,3aα,4β,7aβ)]]]-3-[2-(Octahydro-4-hydroxy-7a-methyl-1H-inden-1-yl)propyl]-2,2-dimethyl-4, 5-isoxazolidinedicarboxylic acid dimethyl ester A mixture of 7.60 g (30 mmol) of [1R-[1α(R*,Z),3aβ,-4α,7aα]]-octahydro-7a-methyl-1-]1-methyl-3-(methylimino)propyl]-1H-inden-4-ol N-oxide, 5.70 g (36 mmol) of methyl mesaconate, and 4 mL of xylenes was heated in a 140° oil bath. The solution, which formed within 5 min, was heated for 1 hr and then was cooled to room temperature. Chromatography (silica gel, CH₂Cl₂/EtOAc, 2:1) afforded 5.42 g (44%) of [3S,4S,5S[3β,4α,5β(2R*),1R*(1β,3aα,4β,7β) ]]]-3-[2-(octahydro-4-hydroxy-7a-methyl-1H-inden-1-yl) -propyl]-2,2-dimethyl-4,5-isoxazolidinedicarboxylic acid dimethyl ester (oil).

An analytical sample gave Calcd for $C_{22}H_{37}NO_6$: C, 64.21; H, 9.06; N, 3.40. Found: C, 64.35; H, 9.25; N, 3.38. $[\alpha]^{25}$ D= +126.4° (c 0.911, CHCl₃); m/e 411.

EXAMPLE 17

Preparation of [3S,4R,5S[3β,4α,5β[(2R*),1R*(1β,3aα,4β,7aβ)]]]-3-[2-(Octahydro-4-hydroxy-7a-methyl-1H-inden-1-yl) propyl]-2,2-dimethyl-4,5-isoxazolidinedimethanol A solution of 10.53 g (25.6 mmol) of [3S,4S,5S[3β,4α,5β[(2R*),1R* (1β,3aα,4β,7aβ)]]]-3-[2-(2-(octahydro-4-hydroxy-7a-methyl-1H-inden-1-yl)propyl]-2,2-dimethyl-4, 5-isoxazolidinedicarboxylic acid dimethyl ester, in 30mL of dry THF was added dropwise over 30 min (argon atmosphere) to a stirred suspension of 4.85 g (129 mmol) of lithium aluminum hydride in 150 mL of dry THF maintaining the temperature between 3° and 8° by means of an ice bath. The suspension was allowed to stir for 1 hr (at 4°) and then 6 mL of water followed by 4 mL of 1N NaOH were cautiously added. Stirring was continued for about 15 min. The suspension was filtered through a glass microfibre filter (Whatman). The filter cake was washed with 6×25 mL of THF. The combined filtrates, on evaporation of the solvent, afforded 8.32 g of solid residue. The filter cake still contained product and was added to 250 mL of 20% Rochelle salt solution, stirred for 1 hr, and then extracted with 3×150 mL of ethyl acetate. The combined organic phases were dried (Na₂SO₄), filtered, and evaporated to give an addition 0.70 g of residue. Thus, the total of crude [3S,4R,5S[3β,4α,5β[(2R*),1R* 1β,3aα,4β,7aβ)]]]-3-[2-(octahydro-4-hydroxy-7a-methyl-1H-inden-1-yl)propyl]-2, 2-dimethyl-4,5-isoxazolidinedimethanol amounted to 9.02 g (99%).

An analytical sample, obtained after LC (silica gel, EtOAc/MeOH, 95:5) and recrystallization, had m.p. 151°-152° (EtOAc). Calcd for $C_{20}H_{37}NO_4$: C, 67.57; H, 10.49; N, 3.94. Found: C, 67.26; H, 10.56; N, 3.72. $[\alpha]^{25}$ D+108.4° (c 0.944, CHCl₃), m/e 355.

EXAMPLE 18

Preparation of [1R-[1α(3R*,4S*,5R*,6S*),3aβ,4α,7aα]-6-Octahydro-4-hydroxy-7a-methyl-1H-inden-1-yl) -4-(dimethylamino)-3-hydroxymethyl-2-methylheptane-1,2-diol A solution of [3S,4R,5S[3β,4α,5β[(2R*),1R*(1β,-3aα,4β,7aβ)]]]-3-[2-(octahydro-4-hydroxy-7a-methyl-1H-inden-1-yl) propyl]-2,2-dimethyl-4,5-isoxazolidinedimethanol from the previous experiment and 2.5 mL (38 mmol) of freshly distilled methyl iodide in 10 mL of dry THF and 50 mL of toluene was heated at 60° (bath) for 3.5hr and then was evaporated to dryness (aspirator). The crude methiodide was dissolved in 250 mL of 50% aqueous acetic acid with warming and stirring. After the solution was cooled to room temperature, 9.0g (137 mmol) of zinc dust was added. The suspension was stirred overnight and the residual zinc was removed by filtration and was washed (aq. HOAc). The pH of the filtrate was adjusted to 11 with 230 mL of conc. ammonium hydroxide. Extraction with 3×300 mL of CH₂Cl₂, 2×300 mL of ether, 2×250 mL of 4:1 CH₂Cl₂/i-PrOH gave 8.7 g of crude [1R-[1α(3R*,4S*,5R*,6S*),3aβ,4α,7aα]-6-octahydro-4-hydrox-7a-methyl-1H-inden-1-yl) -4-(dimethylamino)-3-hydroxymethyl-2-methylheptane-1,2-diol. Recrystallization from 350 mL of CH₂Cl₂ gave 5.90 g of crystals. The mother liquors afforded, after chromatography (silica gel, EtOAc/MeOH/Et₃N₉ 94:1:5), 1.62 g for a total of 7.52 g (81% yield) of the product.

An analytical sample had, m.p. 178°-180° (CH₂Cl₂) Calcd for $C_{21}H_{41}NO_4$: C₉ 67.88; H, 11.12; N, 3.77. Found: C, 67.61; H, 11.06; N₉ 3.78. $[\alpha]^{25}$ D+21.7° (c 0.986, CHCl₃).

EXAMPLE 19

Preparation of 1R-[1α(1R*,3S*,4R*)[4S*],3aβ,4α,7aα]]-Octahydro-7a-methyl-1-[3-(dimethylamino)-4-hydroxy-methyl-1-methyl-4-(2,2, 4-trimethyl-1,3-dioxolan-4-yl)butyl]-1H-inden-4-ol The addition of 3.0 g (15.8 mmol) of p-toluenesulfonic acid monohydrate to a suspension of 4.90 g (13.2 mmol) of [1R-[1α(3R*,4S*,5R*,6S*), 3aβ,4α,7aα]]-6-octahydro-4-hydroxy-7a-methyl-1H-inden-1-yl) -4-(dimethylamino)-3-hydroxymethyl-2-methylheptane-1,2-diol in 75 mL of acetone and 4.9 mL of dimethoxypropane at room temperature produced a clear solution which was stirred (argon atmosphere) for 17 hrs. Then, 8 mL of 2N NaOH was added and the mixture was concentrated with a rotary evaporator (reduced pressure). The residual aqueous suspension was extracted with 4×100 mL of methylene chloride. The combined organic phases were dried (Na₂SO₄), filtered, and evaporated to give 5.7 g of crude product. Purification by medium pressure LC (silica gel, hexanes/EtOAc/Et₃N₉ 60:30:5) gave 4.79 g (88%) of [1R-[1α(1R*,3S*,4R*)[4S*], 3aβ,4α,7aα]]-octahydro-7a-methyl-1-[3-(dimethylamino) -4-hydroxy-methyl-1-methyl-4-(2,2,4-methyl-1,3-dioxolan-4-yl) -butyl]-1H-inden-4-ol.

An analytical sample had m.p. 104°-105° (pentane/ether, 2:1). Calcd for $C_{24}H_{45}NO_4$: 70.03; H, 11.02; N, 3.40. Found: C, 69.97; H, 10.96; N, 3.39. $[\alpha]^{25}$ D+19.5° (c 0.943, CHCl₃).

EXAMPLE 20

Preparation of [1R-[1α(1R*,E,4R*),[4S*],3aβ,4α,7aα]]-Octahydro-7a-methyl-1-[4-(hydroxymethyl)-1-methyl-4-[(2,2, 4-trimethyl-1,3-dioxolan-4-yl)-2-butenyl-1Hinden-4-ol A solution of [1R-[1α(1R*,3S*,4R*)[4S*],3aβ,4α,-7aα]]-octahydro-7a-methyl-1-[3-(dimethylamino) -4-hydroxymethyl-1-methyl-4-(2,2,4-trimethyl-1,3-dioxolan-4-yl)-butyl]-1H-inden-4-ol and 0.5 mL (7.5 mmol) of freshly distilled methyl iodide in 20 mL of dry toluene and 50 mg of potassium carbonate (anhydrous) was heated at 65° (bath) for 16 hr (argon atmosphere) An additional 0.5 mL (7.5 mmol) of freshly distilled methyl iodide was added and heating continued for 4.5 hr. The reaction mixture was evaporated (reduced pressure) to give the crude methiodide (2.83 g).

To the above residue was added 10 mL of dry t-butanol and 1.12 g (10 mmol) of potassium t-butylate, and the reaction mixture was heated (argon atmosphere) at 55° for 24 hrs, then at reflux (100° bath) for 5 hrs. The t-butanol was removed on a rotary evaporator. To the residue was added 10 mL of water followed by extraction with 3×50 mL of ether. The combined extracts were dried (Na$_2$SO$_4$), filtered, and evaporated to give 1.63 g of crude product. Medium pressure LC (silica gel, CH$_2$Cl$_2$/EtOAc, 1:1) gave 881 mg (48%) of [1R-[1α(1R*,E,4R*), [4S*],3aβ,4α,7aα]]-octahydro-7a-methyl-1-[4-(hydroxymethyl)-1-methyl-4-[(2,2,4-trimethyl-1,3-dioxolan-4-yl)-2-butenyl]-1H-inden-4-ol.

EXAMPLE 21

Preparation of
[1R-[1α(1R*,E,4R*),[4S*],3aβ,4α,7aα]]-Octahydro-7a-methyl-1[1-methyl-4-[[4-(methylphenyl)sulfonyl]oxymethyl]-4-(2,2,4-trimethyl-1,3-dioxolan-4-yl)-2-butenyl]-1H-inden-4-ol To a magnetically stirred solution of 742 mg (2.0 mmol) of [1R-[1α(1R*,E,-4R*), [4S*],3aβ,4α,7aα]]-octahydro-7a-methyl-1-[4-(hydroxymethyl)-1-methyl-4-[(2,2,4-trimethyl-1,3-dioxolan-4-yl)-2-butenyl]-1H-inden-4-ol and 613 mg (6.0 mmol) of triethylamine in 10 mL of dry methylene chloride, was added at 0° (argon atmosphere) a solution of 385 mg (2.0 mmol) of p-toluenesulfonyl chloride (TsCl) in 4 mL of methylene chloride. After 45 min at 0°, the bath was removed. After 5 hr at room temperature an addition of 204 mg (2 mmol) of triethylamine and 385 mg (2 mmol) of TsCl were added. A third addition was made after 22 hr at room temperature of 204 mg of triethylamine and 385 mg of TsCl. After 7 hrs, the reaction was poured into 10 mL of 1N NaOH. After separation of the phases, the aqueous phase was re-extracted with 2×20 mL of methylene chloride. Each extract was washed in a counter-current manner with 10 mL of 1N NaOH. The combined organic extracts were dried (Na$_2$SO$_4$), filtered and evaporated to give 1.35 g of crude product. LC separation (silica gel, hexanes/EtOAc, 2:1) gave 840 mg (80%) of [1R-[1α(1R*,E,4R*),[4S*],3aβ,4α,7aα]]octahydro-7a-methyl-1-[1-methyl-4[[(4-methylphenyl)sulfonyl]oxy]methyl]-4-[(2,2,4-trimethyl-1,3-dioxolan-4-yl)-2-butenyl]-1H-inden-4-ol.

EXAMPLE 22

Preparation of
[1R-[1α(1R*,E,4S*),[4S*],3aβ,4α,7aα]]-Octahydro-7a-methyl-1-[1,4-dimethyl-4-[(2,2,4-trimethyl-1,3-dioxolan-4-yl)-2-butenyl]-1H-inden-4-ol To a magnetically stirred suspension of 240 mg (6.3 mmol) of lithium aluminum hydride in 15 mL of dry THF (argon atmosphere), was added rapidly a solution of 818 mg (1.57 mmol) of [1R-[1α(1R*,E,4R*),-[4S*],3aβ,4α, 7aα]]-octahydro-7a-methyl-1-[methyl-4]]4-methylphenyl)sulfonyl]oxy]methyl]-4-[(2,2,4trimethyl-1, 3-dioxolan-4-yl)-2-butenyl]-1H-inden-4-ol. The suspension was heated at reflux for 3 hrs, and then was cooled to 0° whereupon 0.4 mL of water followed by 0.6 mL of 1N NaOH were cautiously added. The resulting mixture was stirred for 15 min and then filtered through a glass microfibre filter disc (Whatman). The filter cake was washed with 2×50 mL of THF. The combined filtrates, on evaporation, gave 641 mg of crude product. Chromatography (silica gel, hexanes/EtOAc, 2:1) afforded 498 mg (90%) of [1R-[1α(12*,E,4S*),[4S*], 3aβ,4α,7aα]]-octahydro-7a-methyl-1-[1,4-dimethyl-4-[(2,2,4-trimethyl-1,3-dioxolan-yl)-2-butenyl]-1H-inden-4-ol.

An analytical sample had mp 69–71 (hexanes). Calcd for C$_{22}$H$_{38}$O$_3$: C, 75.38; H, 10.94. Found: C, 75.51; H, 11.01. [α]$^{25}$ D+5.18 (c 1.023, CHCl$_3$).

EXAMPLE 23

Preparation of
[1R-[1β(1R*,2E,4S*),[4S*],3aα,7aβ]]-Octahydro-7a-methyl-1-[1,4-dimethyl-4-[(2,2,4-trimethyl-1,3-dioxolan-4-yl)-2-butenyl]-4H-inden-4-one To a suspension of 1.000 g (3.42 mmol) of 2,2'-bipyridinium chlorochromate and 0.500 g (6.10 mmol) of anhydrous sodium acetate in 10 mL of methylene chloride was added a solution of 0.300 g (0.86 mmol) of [1R-[1β(1R*,2E,4S*),[4S*], 3aα,7aβ]]-octahydro-7a-methyl-1-[1,4-dimethyl-4-[(2,2,4-trimethyl-1,3dioxolan-4-yl)-2-butenyl]-4H-inden-4-ol dissolved in 6 mL of methylene chloride and the mixture obtained stirred at room temperature for 2 hr. Additional 0.500 g (1.71 mmol) of 2,2'-bipyridinium chlorochromate was then added and the stirring continued for an additional 2 hr. After this time, the mixture was treated with 1 mL of 2-propanol and 20 min later, diluted with water and extracted with a 1:1 mixture of ether and ethyl acetate. The combined organic phases were washed with water, dried, evaporated and the residue purified by fast filtration through silica (eluent: hexane-ethyl acetate, 4:1) to give 0.284 g (95%) of [1R-[1β(1R*,2E,4S*),[4S*],3aα,-7aβ]]-octahydro-7a-methyl-1-[1.4-dimethyl-4-[(2,2,4-trimethyl-1,3-dioxolan-4-yl)-2-butenyl]-4H-inden-4-one, [α]$^{25}$ D= −12.1° (c 0.5 in ethanol).

EXAMPLE 24

Preparation of 1α,25S,26-Trihydroxyergocalciferol

A solution of 665 mg (1.14 mmol) of [3S-(3α,5β,Z)]-2-[2-methylene-3,5-bis-(1, 1-dimethylethyl)dimethylsilyloxy]cyclohexylidene]-ethyldiphenyl phosphine oxide in 14 mL of anhydrous tetrahydrofuran was cooled at −78° C. and treated dropwise and under argon with 0.700 mL (1.12 mmol) of a 1.6 molar solution of n-butyllithium in hexane. After stirring for 5 min, a solution of 234 mg (0.671 mmol) of [1R-[1β(1R*,2E,4 S*),[4S*],3aα,7aβ]]-octahydro-7a-methyl-1-[1,4-dimethyl-4-[(2,2,4-trimethyl-1,3-dioxolan-4-yl)-2-butenyl]-4H-inden-4-one in 3 mL of anhydrous tetrahydrofuran was added dropwise to the deep orange phosphinoxy carbanion solution and the resulting mixture stirred at −78° C. for 1.5 hr. It was then treated with 5 mL of a 1:1 mixture of 2N potassium sodium tartrate and 2N potassium bicarbonate solution, allowed to come to room temperature, diluted with water and extracted with ethyl acetate. The combined organic layers were washed with brine, dried and evaporated to dryness. The residue was purified by fast filtration through silica (eluent: hexane-ethyl acetate, 10:1), then dissolved in a mixture of 1.5 mL of methylene chloride and 12 mL of methanol and stirred at room temperature under argon with 7.5 g of AG 509W-X4-cation exchange resin (200–400 mesh, Bio-Rad Laboratories, Richmond, CA) for 18 hr. After filtration of the resin and washing with methanol, the solvent was evaporated and the residue dissolved in ethyl acetate and washed with 1N potassium bicarbonate solution, then brine, dried and evaporated to dryness. The so obtained material was purified by rapid chromatography on silica, eluting with ethyl acetate to give 248 mg (83% yield) of pure 1α,25S,26-trihydroxycholecalciferol, m.p. 186°–187° C.; [α]$^{25}$ D+40.2 (c 0.3 in ethanol); $^1$H NMR (200 MHz, CD$_3$OD) & 0.58 (s, 3H), 0.98 (d, J=7.2 Hz, 3H) 1.06 (d, J=7.6, 3H), 1.08 (s, 3H), 3.40 (AB q, J$_{AB}$=8.4 Hz, Δγ=16.0 Hz, 2H), 4.14 (m,1H), 4.34 (m, 1H), 4.90 (s, 1H), 5.26 (dd, $J_1=8.4$ Hz, $J_2=15.6$ Hz, 1H), 5.29 (s, 1H), 5.45 (dd, $J_1=7.9$ Hz, $J_2=15.6$ Hz, 1H), 6.08 (d, $J=11.6$ Hz, 1H), 6.32 (d, $J=11.6$ Hz, 1H).

We claim:

1. A compound selected from the group consisting of $1\alpha,25(S),26$-trihydroxy-$\Delta^{22}$-cholecalciferol and $1,\alpha,25(R),26$-trihydroxy-$\Delta^{22}$-cholecalciferol.

2. A compound selected from the group consisting of $1\alpha,25(S),26$-trihydroxyergocalciferol and $1\alpha,25(R),26$-trihydroxyergocalciferol.

3. In accordance with claim 1, $1\alpha,25(S),26$-trihydroxy-$\Delta^{22}$-cholecalciferol.

4. In accordance with claim 1, $1\alpha,25(R),26$-trihydroxy-$\Delta^{22}$-cholecalciferol.

5. In accordance with claim 2, $1\alpha,25(R),26$-trihydroxyergocalciferol.

6. In accordance with claim 2, $1\alpha,25(R),26$-trihydroxyergocalciferol.

7. A pharmaceutical composition useful for treating leukemia which comprises an effective amount of a compound selected from the group consisting of $1\alpha,25(S),26$-trihydroxy$\Delta^{22}$-cholecalciferol, $1\alpha,25(R),26$-trihydroxy-$\Delta^{22}$-cholecalciferol, $1\alpha,25S,26$-trihydroxyergocalciferol and $1\alpha,25R,26$-trihydroxyergocalciferol, in combination with a pharmaceutically acceptable carrier material.

8. A pharmaceutical composition, in accordance with claim 7, wherein the compound is $1\alpha,25(S),26$-trihydroxy-$\Delta^{22}$-cholecalciferol.

9. A pharmaceutical composition in accordance with claim 7, wherein the compound is $1\alpha,25S,26$-trihydroxyergocalciferol.

10. A method of treating leukemia which comprises orally or parenterally administering to a warm-blooded animal requiring such treatment an effective amount of a compound selected from the group consisting of $1\alpha,25(S), 26$-trihydroxy $\Delta^{22}$-cholecalciferol, $1\alpha,25(R), 26$-trihydroxy-$\Delta^{22}$-cholecalciferol, $1\alpha,25S,26$-trihydroxyergocalciferol and $1\alpha,25R,26$-trihydroxyergocalciferol.

11. A method, in accordance with claim 10, wherein the compound is $1\alpha,25(S),26$-trihydroxy-$\Delta^{22}$-cholecalciferol.

12. A method, in accordance with claim 10, wherein the compound is $1\alpha,25S,26$-trihydroxyergocalciferol.

13. A method, in accordance with claim 10, wherein the compound is $1\alpha,25R,26$-trihydroxyergocalciferol.

* * * * *